United States Patent [19]

Billenstein et al.

[11] 4,209,456

[45] Jun. 24, 1980

[54] FLUORINE-CONTAINING ALKYL-SULFATO-BETAINES AND PROCESSES FOR THEIR MANUFACTURE

[75] Inventors: Siegfried Billenstein, Burgkirchen; Winfried Ehrl, Neuötting, both of Fed. Rep. of Germany

[73] Assignee: Hoechst Aktiengesellschaft, Fed. Rep. of Germany

[21] Appl. No.: 956,870

[22] Filed: Nov. 1, 1978

[30] Foreign Application Priority Data

Nov. 4, 1977 [DE] Fed. Rep. of Germany ....... 2749329

[51] Int. Cl.[2] ............ C07C 141/10

[52] U.S. Cl. ............ 260/458 F; 260/458 R

[58] Field of Search ............ 260/458 R, 458 F

[56] References Cited

U.S. PATENT DOCUMENTS

| | | | |
|---|---|---|---|
| 2,803,656 | 8/1957 | Ahlbrecht et al. | 260/458 F |
| 3,390,167 | 6/1968 | Bender et al. | 260/458 R |
| 3,839,343 | 10/1974 | Anello et al. | 260/458 F |

*Primary Examiner*—Norman Morgenstern
*Assistant Examiner*—Vera C. Clarke
*Attorney, Agent, or Firm*—Connolly and Hutz

[57] ABSTRACT

Fluorine-containing alkyl-sulfato-betaines of the formula $$R_f-(CF=CH)_m-(CH_2)_p-\overset{R^1}{\underset{R^2}{N^{\oplus}}}-Q-SO^{\ominus}O_3,$$

in which $R_f$ is perfluoroalkyl with 3 to 16 C atoms, $R^1$ is alkyl with 1 to 4 C atoms, $R_2$ is alkyl with 1 to 4 C atoms, Q is $-CH_2-CH_2-$ or $$-CH_2-\underset{CH_3}{CH}-,$$

m is numbers 0 or 1 and, if m is 0, p is an integer from 1 to 4 and, if m is 1, p is the number 1, are prepared by reacting a compound of the formula $$R_f-(CF=CH)_m-(CH_2)_p-\overset{R^1}{N}-Q-OH$$

in which $R_f$, Q, m and p are as defined above, with at least one known sulfating agent at $-30$ to $+60°$ C. in the presence of at least one solvent (a) which dissolves the abovementioned amine and does not react with the sulfating agent, dissolving the resulting product, after removing the solvent (a), in at least one polar solvent (b), neutralizing the solution with at least one known alkali and then reacting the neutral solution at 40 to 130° C. and under a pressure of about 1 to about 6 bars with a compound of the formula $R_2Z$, in which Z is Cl, Br, I or $-OSO_2OR^2$ and $R^2$ is as defined above.

9 Claims, No Drawings

FLUORINE-CONTAINING ALKYL-SULFATO-BETAINES AND PROCESSES FOR THEIR MANUFACTURE

The invention relates to fluorine-containing alkyl-sulfato-betaines and processes for their manufacture.

The manufacture of sulfatoethyl- or sulfatopropyl-betaines which carry one longer chain and two short chain alkyl groups on the nitrogen atom and do not contain fluorine is known. Such compounds are obtained when the tertiary amine which contains one longer chain and two short chain alkyl groups is first reacted with ethylene-chlorohydrin or with 3-chloro-1-propanol and the 2-hydroxy-trialkylammonium chloride thus formed is reacted with chlorosulfonic acid, it also being possible analogously to use the 3-hydroxy-propyl-trialkylammonium chloride. If it is attempted to react trialkylamines which contain a longer chain fluorine-containing alkyl or alkenyl radical (for example a 1,1,2,2-tetrahydro-perfluorodecyl or a 1,1,2-trihydro-prefluorodecen-2-yl radical) in the same way, a mixture of very diverse and in some cases polymeric compounds is obtained, from which it is difficult to isolate individual substances. Difficulties also arise since the fluorine-containing amines reacted, for example, with chloroethanol dissolve to only an inadequate extent in those solvents which are suitable for the sulfation.

Furthermore, it is known to react tertiary alkylamines which do not contain fluorine with, for example, sodium 1-chlorobutyl-4-sulfate with the elimination of NaCl to give the sulfobetaine. When this process is applied to fluorine-containing tertiary alkylamines, however, poor yields are found and also difficulties arise due to the ease with which the compounds formed decompose are found and as a result of this only highly impure products can be obtained.

The present invention relates to fluorine-containing alkyl-sulfato-betaines of the formula $$R_f-(CF{=}CH)_m-(CH_2)_p-\overset{\displaystyle R^1}{\underset{\displaystyle R^2}{\overset{|}{\underset{|}{N^{\oplus}}}}}-Q-O\overset{\ominus}{S}O_3, \qquad (I)$$

in which $R_f$ denotes a perfluoroalkyl radical with 3 to 16 and preferably 5 to 12 C atoms, $R^1$ denotes an alkyl radical with 1 to 4 and preferably 1 or 2 C atoms, $R^2$ denotes an alkyl radical with 1 to 4 and preferably 1 or 2 C atoms, Q denotes the alkylene radicals $-CH_2CH_2-$ or $$-CH_2-\underset{\displaystyle CH_3}{\underset{|}{CH}}-,$$

preferably the alkylene radical $-CH_2CH_2-$, m denotes the numbers 0 or 1 and, if m is 0, p is an integer from 1 to 4, preferably the number 2 to 4, and if m is 1, p is the number 1.

Particularly preferred compounds of the formula (I) are those in which $R_f$, $R^1$, $R^2$ and Q are as defined above or have the preferred meaning and m is 1 and p is 1.

The invention also relates to a process for the manufacture of the compounds described above, which comprises first reacting a compound of the formula $$R_f-(CF{=}CH)_m-(CH_2)_p-\overset{\displaystyle R^1}{\overset{|}{N}}-Q-OH \qquad (II)$$

in which $R_f$, Q, m and p are as defined above, with at least one known sulfating agent at $-30°$ to $+60°$ C. in the presence of at least one solvent (a) which dissolves the abovementioned amine and does not react with the sulfating agent, dissolving the resulting product, after removing the solvent (a), in at least one polar solvent (b), neutralizing the solution with at least one known alkali and then reacting the neutral solution at 40° to 130° C. and under a pressure of about 1 to about 6 bars with a compound of the formula $R_2Z$, in which Z is Cl, Br, I or $-OSO_2OR^2$ and $R^2$ is as defined above.

The fluorinated amines employed as starting compounds can be manufactured, for example, by the processes described in U.S. Pat. No. 3,535,381, German Offenlegungsschrift No. 1,768,939 or German Offenlegungsschrift No. 2,141,542.

Examples of suitable sulfating agents are concentrated sulfuric acid, solutions of sulfur trioxide in concentrated sulfuric acid (oleum) and also, in particular, chlorosulfonic acid and sulfur trioxide. The latter is advantageously used as a gaseous admixture to inert gases, such as, for example, nitrogen or air. These gas mixtures can contain about 0.5 to 10% by volume of $SO_3$. The sulfation is advantageously carried out at temperatures between 0° and 30° C. The pressure employed for this reaction is not critical. In general, the reaction is carried out at atmospheric pressure but a slight excess pressure of up to about 2 bars can also be used. It is also possible to use a lower reduced pressure of down to about 0.3 bar as long as the solvent (a) used does not yet boil under the reaction conditions chosen.

Suitable solvents (a) are halogenated hydrocarbons with 1 to 2 C atoms, especially carbon tetrachloride, chloroform or methylene chloride; or fluoro-chlorohydrocarbons with 1 up to about 3 C atoms, especially 1,1,2-trifluoro-1,2,2-trichloroethane; and also, in particular, acetonitrile or liquid sulfur dioxide. It is possible to use either a single solvent from amongst those mentioned or to use several of the said solvents in a mixture with one another.

Depending on the temperature used and the reactants employed, the sulfation in general takes between 1 and 10 hours. A slight excess of the sulfating agent over the stoichiometrically calculated amount is generally desirable.

The solvent (a) is approximately so chosen that the sulfated amine is substantially insoluble therein. After the sulfation reaction has ended, the insoluble product formed is filtered off, washed with the solvent (a) and appropriately dried under a reduced pressure of about 1 to about 990 mbars and at a somewhat elevated temperature of 25° to about 80° C.

The product thus obtained is dissolved in a polar solvent (b) and the solution is neutralized, with cooling if necessary. Examples of suitable polar solvents (b) are: aliphatic monoalcohols with 1 to 6 C atoms, preferably methanol, ethanol, isopropanol or n-butanol, or aliphatic ether-alcohols with 3 to 6 C atoms, such as dimethylglycol, ethylglycol, butylglycol, diglycol, methyldiglycol or glycol, or water. It is possible to use either a single solvent from amongst those mentioned or to use several of the said solvents in a mixture with one another. Known alkalis are used for the neutralization, preferably sodium hydroxide, potassium hydroxide or the sodium alcoholates or potassium alcoholates of monohydric aliphatic alcohols with 1 to 4 C atoms. The hydroxides are preferably used as a solution in water and the alcoholates are preferably used as a solution in the alcohol which forms the alcoholate component. The neutralization is monitored with known acid/base indicators, such as, for example, phenolphthalein or Methyl Orange.

The neutralized solution is now reacted at a temperature of 40° to 130° C. and under a pressure of about 1 to about 6 bars with known alkylating agents. The temperature and pressure are preferably so adjusted that the solvent (b) or solvent mixture boils.

The alkylating agents used are compounds of the formula $R^2Z$ in which $R^2$ is as defined above and Z is Cl, Br, I or $—OSO_2OR^2$. Methyl iodide, methyl chloride and dimethyl sulfate are preferably used. In the case of alkylating agents which are gaseous under normal pressure, such as methyl chloride, methyl bromide and ethyl chloride, elevated pressure is appropriately employed. The time necessary for the alkylation varies depending on the temperature used and the starting materials used; in general, the alkylation has ended after about 2 to 4 hours. The alkylating agent is appropriately employed in stoichiometric amounts and a slight excess is sometimes advantageous.

For some purposes, the solution obtained after the alkylation can already be used as such, after removal of the excess alkylating agent if necessary. If the pure, solid, fluorinated alkyl-sulfato-betaines of the formula I are desired, the solvent (b) is distilled off after the alkylation and if appropriate the distillation is carried out under reduced pressure and at slightly elevated temperature (conditions as indicated above). Either before or after separation of a certain amount of the solvent (b), the residual liquid can be separated off from some of the salts contained therein, such as sodium chloride, sodium iodide or sodium methylsulfate, by filtration. For final purification of the crude product freed from the solvent (b), this product is recrystallized from solvents (c), such as, for example, methanol, ethanol, isopropanol, water or mixtures thereof.

The process according to the invention makes it possible to manufacture fluorine-containing alkyl-sulfato-betaines of the formula I in good purity and in high yields. The process parameters to be used make it possible to carry out the process without expensive special apparatuses. The sulfating agents, alkylating agents and solvents to be used are inexpensive and make possible a procedure which is technically uncomplicated and economically of interest.

The fluorine-containing alkyl-sulfato-betaines of the formula I, according to the invention, are distinguished by high surface-activity. Coupled with the compatibility with cationic, non-ionic or anionic surface-active agents, they are suitable for use in the manufacture of polytetrafluoroethylene dispersions, especially of dispersions of polytetrafluoroethylene which have a low or medium molecular weight (so-called polytetrafluoroethylene waxes), as flow control agents for waxes, as cleaning assistants in dry-cleaning and also, in particular, as mixing components in fire extinguishing substances.

The examples which follow are intended to illustrate the invention in more detail:

EXAMPLE 1

496 g of (N-1,1,2-trihydroperfluorodecen-2-yl)-N-methylethanolamine are dissolved in one liter of carbon tetrachloride (a) and 165 l of a sulfur trioxide/air mixture which contains 9% by volume of $SO_3$ are introduced into the solution in the course of 2 hours, with stirring and whilst maintaining a temperature of 30° C. The acid sulfuric acid ester formed precipitates as a solid. It is filtered off, dried under 20 mbars and at 50° C. and then dissolved in one liter of isopropanol (b) and the solution is neutralized with 127 g of a 30% strength by weight solution of sodium methylate in methanol. 126 g of dimethyl sulfate are added to the neutral solution and the mixture is stirred for 4 hours at 60° C. and then filtered at about 50° C. The filtrate is cooled to 0° C. and the solid which has precipitated is filtered off and recrystallized from isopropanol (c). 478 g of a product of the formula given below are isolated and this corresponds to a yield of 81% of the theoretical value. Elemantary analysis gave the following values (calculated theoretical values in brackets): C 27.9% (28.4%), H 2.1% (2.2%), N 2.4% (2.4%), S 5.2% (5.4%). This corresponds to the formula

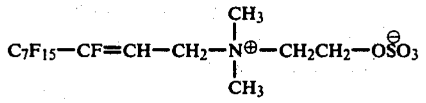

EXAMPLE 2

The procedure described in Example 1 is followed except that 142 g of methyl iodide are added in place of the dimethyl sulfate. After recrystallization, this gives 348 g, corresponding to a yield of 67% of the theoretical value, of a compound for which the values determined by elementary analysis and also the IR and NMR spectra agree with those of the product which was obtained in Example 1.

EXAMPLE 3

(a) 496 g of (N-1,1,2-trihydroperfluorodecen-2-yl)-N-methylethanolamine are dissolved in 0.5 liter of acetonitrile (a) and 116.5 g of chlorosulfonic acid are added dropwise in the course of 30 minutes, with stirring, at 30° to 40° C. The mixture is then filtered and the resulting filter cake is washed with twice 100 ml of acetonitrile and then dried under 20 mbars and at 50° C. This gives 507 g, corresponding to a yield of 88% of the theoretical value, of the inner salt of the ethanolamine sulfate of the following formula:

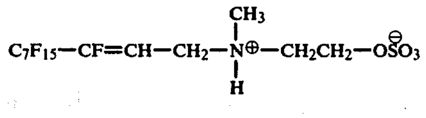

Elementary analysis gave the following values (theoretical values in brackets):

C 26.6% (26.9%); H 2.2% (1.6%); S 5.6% (5.5%); N 2.4% (2.4%); Cl<0.1% (0%).

(b) 507 g of the sulfation product obtained as described above are dissolved in 1.35 liters of isopropanol (b) and the solution is neutralized with 38.8 g of a 50% strength by weight aqueous solution of sodium hydroxide, with stirring. The mixture is then warmed to 60° C.

for several minutes and is then filtered at 50° C. and the resulting filtrate is concentrated to ¼ of its volume. After cooling the concentrated filtrate to 0° C., the crystals which have formed are filtered off and dried. This gives 412 g, corresponding to 79% of the theoretical value, of a compound of the following formula:

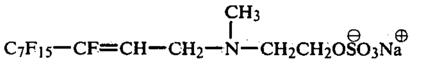

Elementary analysis gave the following values (theoretical values in brackets):

C 25.4% (25.9%); H 2.2% (1.7%); N 2.2% (2.3%); Na 3.6% (3.8%); S 5.0% (5.3%); Cl<0.1% (0%).

(c) 412 g of the neutralized sulfation product which has been obtained as described under (b) are dissolved in 500 ml of isopropanol (b) and 94 g of dimethyl sulfate are added dropwise in the course of 30 minutes, with stirring. The mixture is then boiled under reflux for 4 hours and then filtered at 50° C. After cooling the filtrate to 0° C., the product which has precipitated is filtered off and dried under 20 mbars and at 50° C. This gives 250 g, corresponding to 62% of the theoretical value, of a compound of the formula

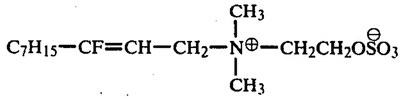

Elementary analysis gave the following values (theoretical values in brackets):

C 28.1% (28.4%); H 2.2% (2.2%); N 2.4% (2.4%); S 5.2% (5.4%).

EXAMPLE 4

An (N-1,1,2-trihydroperfluoroalken-2-yl)-N-methylethanolamine in which the perfluorinated alkyl radical $R_f$ consists of a mixture of different perfluorinated alkyls of the following composition: 41% by weight of $C_5F_{11}$-, 40% by weight of $C_7F_{15}$—, 14% by weight of $C_9F_{19}$— and 5% by weight of $C_{11}F_{23}$, used.

948 g of the compound described above, which has an amine number of 20.2, are dissolved in 1.6 l of carbon tetrachloride (a) and 165 l of a $SO_3$/air mixture which contains 9% by volume of $SO_3$ are passed in in the course of 2 hours at 20° C. and atmospheric pressure, the acid sulfuric acid ester formed precipitating as a solid. After filtering off and drying under 20 mbars and at 50° C., the solid product is dissolved in 1.5 l of methanol (b) and the solution is neutralized with 570 g of a 30% strength by weight methanolic solution of sodium methylate. 250 g of methyl sulfate are then added dropwise to the neutralized solution, with stirring and whilst boiling under reflux, and the mixture is then warmed at 60° C. for 4 hours. After evaporating off the solvent at about 80° C., the residue is dried under 20 mbars and at 50° C. This gives 1,085 g of a product which contains 123 g of sodium methylsulfate (=11.4% by weight). A sample of this product is purified by the column chromatography method described further below. The amount of pure fluorine-containing alkyl-sulfato-betaines determined in this way corresponds to 85% of the theoretical value. The resulting mixture of compounds corresponds to the formula

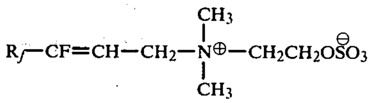

in which $R_f$ corresponds to the mixture of perfluorinated alkyl groups indicated further above.

EXAMPLE 5

The procedure of Example 4 is followed, except that 232 g of chlorosulfonic acid and 1.5 l of chloroform (a) are employed in place of the $SO_3$/air mixture and the carbon tetrachloride. After evaporating off the solvent and drying the residue, 1,100 g of a product which contains 125 g of sodium methylsulfate are obtained. The amount, determined by column chromatography, of the mixture of the purified fluorine-containing alkylsulfato-betaines of the formula indicated in Example 4 corresponds to 84% of the theoretical value.

EXAMPLE 6

948 g of an (N-1,1,2-trihydroperfluoroalken-2-yl)-N-methylethanolamine (amine number 20.2) in which the perfluoroalkenyl radical represents the same mixture of perfluorinated alkyls as described in Example 4, are dissolved in 1.5 liters of chloroform (a) and 232 g of chlorosulfonic acid are added dropwise at 30° C., with stirring. The mixture is then heated slowly to the boil and boiled under reflux for one hour in order to drive off the hydrogen chloride gas formed. After evaporating off the chloroform under 20 mbars and at 50° C., the product is dissolved in 660 g of isopropanol (b), the solution is neutralized with 166 g of a 50% strength by weight aqueous solution of sodium hydroxide and 250 g of dimethyl sulfate are added in the course of about 30 minutes, with stirring. The reaction mixture is then kept at 60° C. for four hours and then cooled to room temperature and 577 g of water are added. This gives a solution in isopropanol/water which has a solids content of 50% by weight. The solid consists of 12% by weight of sodium methylsulfate and 88% by weight of a mixture of fluorine-containing alkylsulfato-betaines of the formula indicated in Example 4. The content of fluorine-containing alkyl-sulfato-betaines was determined by column chromatography.

EXAMPLE 7

515 g of (N-1,1,2-trihydroperfluorodecen-2-yl)-N-ethyl-ethanolamine are dissolved in 1 liter of carbon tetrachloride (a) and, whilst stirring at 30° C., 165 liters of a $SO_3$/air mixture which contains 9% by volume of $SO_3$ are passed in in the course of 2 hours, the acid sulfuric acid ester formed precipitating as a solid. After filtering off and drying under 20 mbars and at 50° C., the solid product is dissolved in one liter of isopropanol (b) and the solution is neutralized with 180 g of a 30% strength by weight methanolic solution of sodium methylate. After adding 126 g of dimethyl sulfate in the course of about 30 minutes, the reaction mixture is stirred for a further 4 hours at 60° C. and then filtered at 50° C. and the filtrate is cooled to 0° C., whereupon a crystalline product precipitates. The solid which has precipitated is filtered off and recrystallized from isopropanol (c). This gives 450 g, corresponding to 74% of the theoretical value, of a product which has the following formula:

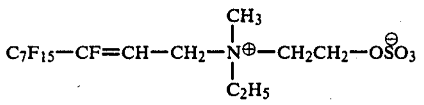

Elementary analysis gave the following values (theoretical values in brackets):

C 29.3% (29.6%); H 2.4% (2.5%); N 2.3% (2.3%); S 5.2% (5.3%).

EXAMPLE 8

520 g of (N-1,1,2,2-tetrahydroperfluorododecyl)-N-methyl-ethanolamine are dissolved in one liter of carbon tetrachloride (a) and 165 liters of a $SO_3$/air mixture which contains 9% by volume of $SO_3$ are passed into the solution in the course of two hours at 30° C., the acid sulfuric acid ester precipitating as a solid. After filtering off and drying under 20 mbars and at 50° C., the solid product is dissolved in one liter of methanol (b) and the solution is neutralized with 180 g of a 30% strength by weight methanolic solution of sodium methylate. 126 g of dimethyl sulfate are added to this solution in the course of 30 minutes and the reaction mixture is then stirred for a further 4 hours at 60° C. and is then filtered at 50° C. and the filtrate is cooled to 0° C. The solid which then precipitates is filtered off and is recrystallized from isopropanol (c). This gives 522 g, corresponding to 85% of the theoretical value, of a compound of the following formula:

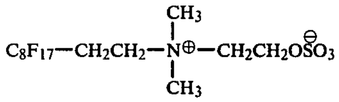

Elementary analysis gave the following values (theoretical values in brackets):

C 27.4% (27.3%); H 2.5% (2.3%); N 2.2% (2.3%); S 5.0 % (5.2%).

The purification of the fluorine-containing alkyl-sulfato-betaines of the formula I to remove impurities is carried out by column chromatography as follows:

A vertical glass tube with an internal diameter of 30 mm is closed at its lower end by a glass frit. The tube is filled to a height of 130 mm with about 30 g of a silica gel which has a grain size of 0.1–0.2 mm and contains about 6% of water (for example of the type MN from Messrs. Macherey und Nagel). 300 to 500 mg of the sulfobetaine to be purified are weighed out, as the sample, and dissolved in 5 ml of analytical grade methanol and the solution is then introduced into the column filled with silica gel and then rinsed with further analytical grade methanol. The first 150 ml of methanolic solution which issue from the bottom of the column are collected and evaporated to dryness, the residue is again taken up in methanol and the solution is filtered through a glass frit which has been covered with filter flock mass. The filtrate is evaporated and the residue is dried for 60 minutes at 105° C. in air. The product thus obtained represents virtually the total amount of the sulfatobetaine contained in the sample. It is possible to check the sulfatobetaine thus obtained in respect of its purity and chemical composition by means of IR or NMR spectra and also by means of thin layer chromatography.

The following NMR spectra were determined for the fluorinated alkyl-sulfato-betaines of the formula I prepared according to Example 1 and 3 c:

$^1$H-NMR spectra in $D_3COD$ (using tetramethylsilane as the internal standard)

| | | | |
|---|---|---|---|
| δ CF=$\underline{CH}$—$CH_2$—N | 6.43 ppm | $J_{FCCH}$=31Hz $J_{HCCH}$=8Hz | (1H) |
| δ CF=CH—$\underline{CH_2}$—N | 4.46 ppm | $J_{HCCH}$= 8Hz | (2H) |
| δ $\underline{CH_3}$ | 3.34 ppm | | (6H) |
| δ N—$\underline{CH_2}$—$CH_2$—O | 3.64 ppm | $J_{HCCH}$= 5Hz | (2H) |
| δ N—$CH_2$—$\underline{CH_2}$—O | 4.06 ppm | $J_{HCCH}$= 5Hz | (2H) |
| (1 ppm = 60 Hz) | | | |

As an example of the good surface-activity of the compounds according to formula I, a comparative measurement of the surface tension of the compound, according to the invention, of Example 1 compared with that of a conventional commercially available fluorine-containing surface-active agent of the formula

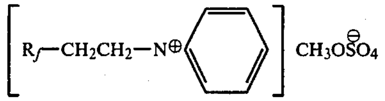

in which $R_f$ is a mixture of perfluorinated alkyl radicals with 6 to 12 carbon atoms, is given below. The measurement was carried out by the ring method (DIN draft 53,914) on aqueous solutions of the substances at 20° C. The surface tension is given in mN/m and the concentration of the surface-active agent is given in grams per liter (g/l).

Furthermore, the compatibility with anionic and cationic surface-active agents was determined. The values measured are given in the table below, a plus sign indicating compatibility and a minus sign indicating incompatibility.

Table

| Surface-active agent | Electrochemical character | Surface tension at a concentration of | | | | Compatibility with other surface-active agents | |
|---|---|---|---|---|---|---|---|
| | | 1 g/l | 0.3 g/l | 0.1 g/l | 0.03 g/l | anionic | cationic |
| According to Example 1 | amphoteric | 18.8 | 19.1 | 19.1 | 20.1 | + | + |
| Commercially available, as described above | cationic | 22.0 | 35.0 | 46.0 | 56.0 | − | + |

We claim:

1. Fluorine-containing alkyl-sulfato-betaines of the formula

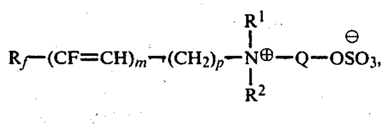

in which $R_f$ denotes a perfluoroalkyl radical with 3 to 16 C atoms, $R^1$ denotes an alkyl radical with 1 to 4 C atoms, $R^2$ denotes an alkyl radical with 1 to 4 C atoms, Q denotes the alkylene radicals $—CH_2CH_2—$ or

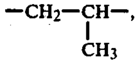

m denotes the numbers 0 or 1 and, if m is 0, p is an integer from 1 to 4 and, if m is 1, p is the number 1.

2. Fluorine-containing alkyl-sulfato-betaines as claimed in claim 1, wherein, in the formula indicated in the said claim, $R_f$ denotes a perfluoroalkyl radical with 5 to 12 C atoms, $R^1$ denotes an alkyl radical with 1 or 2 C atoms, $R^2$ denotes an alkyl radical with 1 or 2 C atoms, Q denotes the alkylene radical $—CH_2CH_2—$, m denotes the numbers 0 or 1 and, if m is 0, p is an integer from 2 to 4 and, if m is 1, p is the number 1.

3. Process for the manufacture of fluorine-containing alkyl-sulfato-betaines as claimed in claim 1, which comprises first reacting a compound of the formula

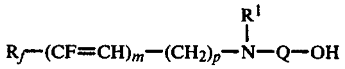

in which $R_f$, Q, m and p are as defined in claim 1, with at least one known sulfating agent at −30° to +60° C. in the presence of at least one solvent (a) which dissolves the abovementioned amine and does not react with the sulfating agent, dissolving the resulting product, after removing the solvent (a), in at least one polar solvent (b), neutralizing the solution with at least one known alkali and then reacting the neutral solution at 40° to 130° C. and under a pressure of about 1 to about 6 bars with a compound of the formula $R_2Z$, in which Z is Cl, Br, I or $—OSO_2OR^2$ and $R^2$ is as defined in claim 1.

4. Process as claimed in claim 3, wherein the sulfating agent employed is sulfur trioxide or chlorosulfonic acid.

5. Process as claimed in any one of claims 3 or 4 wherein the sulfation is carried out at 0° to 30° C.

6. Process as claimed in any one of claims 3 or 4 wherein one or more of the following solvents (a) are employed in the sulfation: carbon tetrachloride, chloroform, methylene chloride, 1,2,2-trichloro-1,1,2-trifluoroethane, aceto-nitrile and liquid sulfur dioxide.

7. Process as claimed in any one of claims 3 or 4 wherein at least one of the following compounds is employed as the polar solvent (b): aliphatic monoalcohols with 1 to 6 C atoms, aliphatic ether-alcohols with 3 to 6 C atoms, glycol or water.

8. Process as claimed in any one of claims 3 or 4 wherein at least one of the following compounds is employed as the alkali: alcoholates of aliphatic monoalcohols with 1 to 4 C atoms or hydroxides of sodium or potassium.

9. Process as claimed in any one of claims 3 or 4 wherein the neutral solution is reacted with methyl iodide, methyl chloride or dimethyl sulfate.

* * * * *